US005932597A

United States Patent [19]
Brown

[11] Patent Number: 5,932,597
[45] Date of Patent: Aug. 3, 1999

[54] ANAESTHETIC FORMULATION

[75] Inventor: Stephen Brown, Cambridge, United Kingdom

[73] Assignee: Darwin Discovery Limited, United Kingdom

[21] Appl. No.: 09/195,908

[22] Filed: Nov. 19, 1998

[30] Foreign Application Priority Data

Nov. 19, 1997 [GB] United Kingdom .................... 9724506
Aug. 19, 1998 [GB] United Kingdom .................... 9818109

[51] Int. Cl.$^6$ ........................ A61K 31/445; C07D 401/00
[52] U.S. Cl. ............................................. 514/330; 546/189
[58] Field of Search .............................. 546/189; 514/330

[56] References Cited

FOREIGN PATENT DOCUMENTS 9000390  1/1990  WIPO .
9510276  4/1995  WIPO .
9510277  4/1995  WIPO .

OTHER PUBLICATIONS

De Paula, M.L., et al. (1997) "Subarachnoid Dispersion of Local Anaesthetics: Consideration in Face of the Advent of Isobaric Bupivacaine" Rev. Bras. Anestesiol. 47(5):439–452 **Abstract No. 287549, Chemical Abstracts 127(21).

Chang, C.J., et al. (1996) "Spinal Anesthesia with 0.25% Hyperbaric Bupivacaine for Cesarean Section: Effects of volume" Br. J. Anaesth 77(2):145–149 ** Abstract No. 185717, Chemical Abstracts 125(15).

Ganem, E.M.., et al. (1996) "Neurotoxicity of Subarachnoid Hyperbaric Bupivacaine in Dogs" Reg. Anesth. 21(3):234–238 **Abstract No. 49134, Chemical Abstracts 125(5).

Hampl, K.F., et al. (1995) "Hyperosmolarity Does Not Contribute to Transient Radicular Irritation After Spinal Anesthesia with Hyperbaric 5% Lidocaine" Reg. Anesth. 20(5):363–368 **Abstract No. 307201, Chemical Abstracts 124(3).

Tetzlaff, J.E. (1995) "Influence of Baricity on the Outcome of Spinal Anesthesia with Bupivacaine for Lumbar Spine Surgery" Reg. Anesth. 20(6):533–537 **Abstract No. 278937, Chemical Abstracts 124(1).

Bigler, D., et al. (1986) "Double–Blind Evaluation of Intrathecal Hyperbaric and Glucose–Free Bupivacaine on Analgesia and Cardiovascular Function" Reg. Anesth. 11(4):151–155 **Abstract No. 107814, Chemical Abstracts 106(14).

Kytta, J. et al. (1982) "Histophathological Changes in Rabbit Spinal Cord Caused by Bupivacaine" Dep. Anesth. 5(4):85–88 **Abstract No. 46867, Chemical Abstracts 98(7).

Bannister, J. et al. (1990) "Effect of Glucose Concentration on the Intrathecal Spread of 0.5% Bupivacaine" British Journal of Anesthesia 64:232–234.

Burke, D., et al. (1998) "Intrathecal 0.5% Levobupivacaine for Lower Limb Surgery" EuroPain (Abstract).

Finucane, B.T. et al. (1980) "A Double–Blind Comparison of Etidocaine and Lidocaine for IV Regional Anesthesia" **Abstract No.

Gelman, S., Jiri J. Vitek (1980) "Thoracic Epidural Catheter Placement Under Fluoroscopic Control in Moribidly Obese Patients".

Tsai, et al. "Spinal Anesthesia with Bupivacaine for Transurethal Resection of Prostate:Effects of Specific Gravity, Volume and Dose" Ma Tsui Hsueh Tsa Chi Anaestesiologic Sinica 1989, 27 (2) 111–116, Abstract, MEDLINE acc. No. 90013942.

Wallin, G, et al "Influence of Intraperitoneal Anesthesia on Pain on the Sympathoadrenal Response to Abdominal Surgery" Acta Anaesthesiologica Scandanavica, 1988, 32 (7), 553–8.

Primary Examiner—Cecilia J. Tsang
Assistant Examiner—Fabian A. Jameison
Attorney, Agent, or Firm—Saliwanchik, Lloyd & Saliwanchik

[57] ABSTRACT

A pharmaceutically-acceptable aqueous solution which is isobaric or hyperbaric, and isotonic, with respect to cerebrospinal fluid (CSF), comprises a 1-alkyl-N-(2,6-dimethylphenyl)-2-piperidinecarboxamide anaesthetic agent such as bupivacaine or levobupivacaine and a saccharide. If the amount of the anaesthetic agent is no more than 0.75% w/v, a salt or another additional non-saccharide is present. Accordingly, the amount of the saccharide can be kept below that which would provide isotonicity in the absence of the additional non-saccharide.

28 Claims, No Drawings

ANAESTHETIC FORMULATION

FIELD OF THE INVENTION

This invention relates to a new formulation of long-acting local anaesthetics.

BACKGROUND OF THE INVENTION

A known class of long-acting local anaesthetics comprises 1-alkyl-N-(2,6-dimethylphenyl)-2-piperidinecarboxamides. This class includes racemic bupivacaine, levobupivacaine, mepivacaine and ropivacaine. Racemic bupivacaine is widely used, and is available for both epidural and spinal administration.

The effective utility of levobupivacaine in man, in vivo, is evidenced for the first time in WO-A-9510276, WO-A-9510277 and Gristwood et al, Exp. Opin. Invest. Drugs 3(11):1209–12 (1994). The latter documents indicate the potential utility of levobupivacaine in obstetrics, in part at least because of reduced CNS side-effects.

WO 90/00390 discloses aqueous solutions for spinal analgesia, comprising dezocine, bupivacaine and also 5–10% w/v glucose if it is desired that the solution should be hyperbaric. The solutions of the Examples which are hyperbaric are also hypertonic.

Chung et al, Br. J. Anaesth. (1996) 77(2):145–9, discloses the use of hyperbaric solutions containing 0.25% w/v bupivacaine and 5% w/v glucose, for spinal anaesthesia. This was done as part of a study to determine the effect of volume of solution administered.

Hytta et al, Regionale-Anaesthesie (1982) 5:85–8, discloses the use of 0.5% bupivacaine, either "isobaric" (Marcain®) or hyperbaric (8% glucose). The former is presumably plain Marcain® which is in fact hypobaric.

In the U.S., a hyperbaric formulation of bupivacaine is available, comprising 2 ml ampoules of 0.75% bupivacaine (racemate) and 8.25% glucose. The use of 0.75% solutions of racemic bupivacaine is contra-indicated, in obstetrical anaesthesia. The Physician's Desk Reference® carries a "black box" warning.

In Europe, 4 ml ampoules are available which contain 0.5% bupivacaine and about 8% glucose. These formulations are hypertonic, having an osmolality of approximately 500 mOsm/kg.

There are certainly good reasons for including glucose. As reported by Logan et al, Brit. J. Anaesthesia (1986) 58:292–296, plain 0.5% bupivacaine has wide variability in terms of its intrathecal spread, when administered for spinal anaesthesia. A hyperbaric solution containing 8% glucose spreads rapidly but predictably; see Chambers et al, Brit. J. Anaesthesia (1981) 53:279–282.

Bannister et al, Brit. J. Anaesthesia (1990) 64:232–234, reports the effects of intrathecal injection of 0.5% bupivacaine in solutions containing 0.33%, 0.83% or 8% glucose. It is suggested that, whereas using 0.33% glucose resulted in variable blocks as seen using the plain solution, 0.83% glucose is preferable. It is reported that "Making bupivacaine slightly hyperbaric seemed to produce a predictable spinal anaesthetic"; however, formulations comprising 0.5% bupivacaine and 0.83% glucose are in fact hypobaric.

It has apparently been accepted by anaesthetists that a high concentration of glucose is necessary. This is despite the fact that such formulations have been associated with neurotoxicity.

SUMMARY OF THE INVENTION

This invention is based at least in part on the realisation that, in order for a formulation of bupivacaine to be most useful for spinal administration, i.e. at least isobaric and also isotonic with respect to cerebrospinal fluid (CSF), the level of saccharide should be chosen with relation to the amount of bupivacaine, and should be in a range between those previously suggested. The ability to produce an isotonic formulation means that potential exchange of solutes with the cellular material in CSF is avoided.

Investigation of various solutions of levobupivacaine, has shown that, at relatively high concentrations and on the addition of glucose, the total amount of the two compounds alone may be sufficient to provide isotonicity. More particularly, at above 0.75%, the level of glucose can be below 5% w/v, while still providing isobaricity or hyperbaricity. When the concentration of the anaesthetic is lower, the inclusion of an additional non-saccharide compound allows the same combination of parameters to be achieved.

According to the present invention, the beneficial effects of a 1-alkyl-N-(2,6-dimethylphenyl)-2-piperidinecarboxamide such as bupivacaine can be provide in combination with a relatively small amount of glucose and, if necessary, a salt such as NaCl. The glucose provides adequate baricity, whilst the salt makes the composition isotonic. The use of large amounts of glucose is thus avoided, and the risk associated with contact between the composition and plasma or cerebrospinal fluid is reduced.

DESCRIPTION OF THE INVENTION

A solution of the invention will usually be sterile, and typically comprises up to 1% w/v of the anaesthetic, e.g. at least 0.25%, and often 0.5 to 0.75% w/v. An advantage of the use of levobupivacaine over bupivacaine may be the ability to use higher concentrations.

Preferably, a composition of the invention is made up in unit dosages, e.g. of 2 or 3 ml, suitably in a sealed container, e.g. of glass or a transparent plastics material. One preferred formulation comprises 2 ml ampoules or vials of 0.75% levobupivacaine (this compound is described herein for the purposes of illustration only).

Spinal administration may be by any conventional means. The formulation will generally be given to provide anaesthesia and analgesia during surgical procedures and also in Caesarean section and to treat chronic pain.

Levobupivacaine used in the present invention is preferably substantially free of dextrobupivacaine, and is more preferably in at least 90%, and most preferably at least 99%, enantiomeric excess with respect to dextrobupivacaine. Throughout this specification, reference to bupivacaine and its enantiomers includes pharmaceutically-acceptable salts thereof. Such a compound is typically provided as the HCl salt. Any other salt that is present must of course be physiologically-acceptable, and will usually comprise an inorganic cation. For example, it may be an alkali metal salt such as NaCl.

The administration of levobupivacaine over a range of concentration, including those currently used for the racemic drug and higher concentrations, can be carried out for significantly longer periods than at present, again as a result of the reduced side-effects experienced with levobupivacaine. For instance, levobupivacaine can be administered to a patient safely for at least 24 hours, often up to 72 hours, and even for periods of up to a week or a fortnight, or longer. It can, of course, be administered for similar periods already used for the racemic drug, e.g. between 3 and 6 hours.

The following Examples illustrate the invention. These Examples use levobupivacaine; using bupivacaine instead should have no effect on osmolality or baricity, at equimolar concentrations.

EXAMPLE 1

Various aqueous formulations of levobupivacaine ("levo") and dextrose were made. They and their baricity and tonicity (and also the corresponding values for CSF) are given in the following Table.

| Product | Specific Gravity | Osmolality (mOsm/kg) |
| --- | --- | --- |
| CSF | 1.0062–1.0082 | 306 |
| 0.75% Levo + 0 dextrose | 1.001 | 46 |
| 0.75% Levo + 2.2% dextrose | 1.0082 | 170 |
| 0.75% Levo + 8.25% dextrose | 1.029 | 510 |
| 0.5% Levo + 0 dextrose | 1.000 | 32 |
| 0.5% Levo + 2.5% dextrose | 1.0082 | 168 |
| 0.5% Levo + 8.25% dextrose | 1.028 | 488 |

Formulations containing more than 2.2% dextrose with 0.75% (7.5 mg/ml) levobupivacaine, or more than 2.5% dextrose with 0.5% (5.0 mg/ml) levobupivacaine, will be technically hyperbaric in all patients. Such formulations, containing less than 5% dextrose, are hypo-osmolar; a suitable salt (NaCl) is added to make the formulations isotonic.

EXAMPLE 2

An aqueous formulation was prepared comprising 0.5% or 0.75% w/v levobupivacaine, 4% w/v dextrose and 0.15% NaCl. This was an isotonic, hyperbaric composition suitable for spinal administration, to provide safe, effective anaesthesia.

In summary, it has been shown that it is possible to reduce the level of glucose in the formulation whilst maintaining an appropriate degree of baricity. Also by the addition of physiologically-acceptable inorganic salts such as sodium chloride, an osmotically-balanced formulation which is isotonic with CSF and body fluids (approximating to 300 mOSm/kg) has been achieved.

I claim:

1. A pharmaceutically-acceptable aqueous solution which is isobaric or hyperbaric, and isotonic, with respect to cerebrospinal fluid (CSF), and which comprises a 1-alkyl-N-(2,6-dimethylphenyl)-2-piperidinecarboxamide anaesthetic agent and a saccharide, provided that, if the amount of the anaesthetic agent is no more than 0.75% w/v, an additional non-saccharide is present and the amount of the saccharide is below that which would provide isotonicity in the absence of the additional non-saccharide.

2. The solution, according to claim 1, which comprises up to 1% w/v of the anaesthetic agent.

3. The solution, according to claim 1, which comprises more than 0.75% w/v of the anaesthetic agent, and the non-saccharide is absent.

4. The solution, according to claim 1, which comprises up to 0.75% w/v of the anaesthetic agent.

5. The solution, according to claim 4, which comprises 0.5 to 0.75% w/v of the anaesthetic agent.

6. The solution, according to claim 1, wherein said saccharide is glucose.

7. The solution, according to claim 1, which comprises more than 1% w/w of the saccharide.

8. The solution, according to claim 7, which comprises more than 2% w/w of the saccharide.

9. The solution, according to claim 1, wherein said non-saccharide is present and is a salt comprising an inorganic cation.

10. The solution, according to claim 9, wherein said salt is NaCl.

11. The solution, according to claim 1, which is hyperbaric with respect to CSF.

12. The solution, according to claim 1, wherein said alkyl group has 1 to 4 carbon atoms.

13. The solution, according to claim 12, wherein said anaesthetic is bupivacaine.

14. The solution, according to claim 12, wherein said anaesthetic agent is levobupivacaine.

15. A container containing a sterile, pharmaceutically-acceptable aqueous solution which is isobaric or hyperbaric, and isotonic, with respect to cerebrospinal fluid (CSF), and which comprises a 1-alkyl-N-(2,6-dimethylphenyl)-2-piperidinecarboxamide anaesthetic agent and a saccharide, provided that, if the amount of the anaesthetic agent is no more than 0.75% w/v, an additional non-saccharide is present and the amount of the saccharide is below that which would provide isotonicity in the absence of the additional non-saccharide.

16. The container, according to claim 15, wherein said solution comprises up to 1% w/v of the anaesthetic agent.

17. The container, according to claim 15, wherein said solution comprises more than 0.75% w/v of the anaesthetic agent, and the non-saccharide is absent.

18. The container, according to claim 15, wherein said solution comprises up to 0.75% w/v of the anaesthetic agent.

19. The container, according to claim 18, wherein said solution comprises 0.5 to 0.75% w/v of the anaesthetic agent.

20. The container, according to claim 15, wherein said saccharide is glucose.

21. The container, according to claim 15, wherein said solution comprises more than 1% w/w of the saccharide.

22. The container, according to claim 21, wherein said solution comprises more than 2% w/w of the saccharide.

23. The container, according to claim 15, wherein said non-saccharide is present and is a salt comprising an inorganic cation.

24. The container, according to claim 23, wherein said salt is NaCl.

25. The container, according to claim 15, wherein said solution is hyperbaric with respect to CSF.

26. The container, according to claim 1, wherein said alkyl group has 1 to 4 carbon atoms.

27. The container, according to claim 26, wherein said anaesthetic is bupivacaine.

28. The container, according to claim 26, wherein said anaesthetic agent is levobupivacaine.

* * * * *